United States Patent [19]
Fedorov et al.

[11] Patent Number: 5,766,245
[45] Date of Patent: Jun. 16, 1998

[54] INTRAOCULAR LENS FOR CORRECTING MODERATE TO SEVERE HYPERMETROPIA

[75] Inventors: Svyatoslav Nikolayevich Fedorov; Victor Konstantinovich Zuev; Albina Ivanovna Ivashina; Sergei Nikolayevich Bagrov; Aleksandr Aleksandrovich Karavaev; Niaz Fuadovich Saifullin, all of Moscow, Russian Federation

[73] Assignee: Staar Surgical, AG, Switzerland

[21] Appl. No.: 777,445

[22] Filed: Dec. 30, 1996

[51] Int. Cl.⁶ .................................................. A61F 2/16
[52] U.S. Cl. .................................................. 623/6
[58] Field of Search .................................................. 623/6

[56] References Cited

U.S. PATENT DOCUMENTS

| | | |
|---|---|---|
| Re. 33,997 | 7/1992 | Kuzma et al. |
| 4,042,457 | 8/1977 | Kuettner et al. |
| 4,064,008 | 12/1977 | Petersen et al. |
| 4,220,724 | 9/1980 | Berg et al. |
| 4,876,332 | 10/1989 | Tsilibary et al. |
| 4,894,441 | 1/1990 | Menicagli. |
| 5,103,840 | 4/1992 | Kavoussi. |
| 5,192,319 | 3/1993 | Worst .................................................. 623/6 |
| 5,210,182 | 5/1993 | Nasrallah et al. |
| 5,424,408 | 6/1995 | Reeders et al. |
| 5,476,515 | 12/1995 | Kelman et al. |

*Primary Examiner*—Mary Beth Jones
*Attorney, Agent, or Firm*—Klima & Pezzlo, P.C.

[57] ABSTRACT

The present intraocular lens includes a body portion and an optic portion. A thickness of the body portion is between 0.3 to 0.98% of a thickness of the intraocular lens itself which lens includes the body portion and the optic portion, and from 0.011 and 0.015% of a length of the body portion. The thickness of the intraocular lens itself, from 0.095 and 0.192% of the length of the body portion. The diameter of the optic portion is from 0.153 and 0.7% of the length of the body portion. The optic portion can have an anterior surface having a radius of curvature of from 0.29 and 0.967% of the radius of curvature of the posterior surface of said intraocular lens. The lens is implanted by insertion into the posterior chamber of the eye to a position anterior to the natural crystalline lens of the eye. The implanted lens is effective in correcting moderate to severe forms of hypermetropia.

38 Claims, 1 Drawing Sheet

INTRAOCULAR LENS FOR CORRECTING MODERATE TO SEVERE HYPERMETROPIA

FIELD OF THE INVENTION

This invention relates to an intraocular lens and to a method of implanting an intraocular lens in the eye of a patient to correct moderate to severe forms of hypermetropia.

BACKGROUND OF THE INVENTION

Intraocular lenses are known and have been implanted into the human eye to provide vision correction of low-level (mild) hypermetropia only. Accordingly, prior to the present invention, patients suffering from middle to high levels (moderate to severe) hypermetropia (farsightedness) were not suitable candidates for surgical correction.

SUMMARY OF THE INVENTION

The present invention relates to an intraocular lens to correct moderate through severe forms of hypermetropia in a patient suffering therefrom. The lens includes a body portion and an optic portion. Preferably, the present intraocular lens is defined by the following parameters: (1) The thickness of the body portion is from 0.3 to 0.98% of the thickness of the intraocular lens itself which lens includes the body portion and the optic portion, (ratio of body portion thickness to intraocular lens thickness is 0.3 to 0.98:1) and from 0.011 and 0.015% of the length of the body portion (ratio of body portion thickness to body portion length is 0.011 to 0.015:1); (2) The thickness of the intraocular lens including the body portion and the optic portion is from 0.095 and 0.192% of the length of the body portion (the ratio of the intraocular lens thickness to body portion length is 0.095 to 0.192:1); and (3) The diameter of the optic portion is from 0.153 and 0.7% of the length of the body portion (the ratio of the diameter of the optic portion to body portion length is 0.153 to 0.7:1).

The present invention relates to a method of implanting the present intraocular lens in an eye of a patient to correct moderate to severe forms of hypermetropia, includes providing an artificial intraocular lens including any one or more of the parameters recited above (see (1), (2) and (3)) and inserting the intraocular lens into the posterior chamber of the eye to a position anterior to the natural crystalline lens of the eye.

The present invention is further directed to the present intraocular lens where the anterior surface of the optic portion constitutes a surface of rotation of the second degree, e.g. paraboloid or ellipsolid.

The present invention relates to the present intraocular lens where the anterior surface of the optic portion is characterized by a spherical impression, and the ratio between the ray of the concave anterior surface of the optic portion and the ray of the concave posterior surface of the optic portion is between 0.29 and 0.967.

The present invention further relates to the present intraocular lens where the thickness of the body portion is 0.15 mm.

The present invention is directed to the present intraocular lens body portion where the length of body portion is from 10 to 13 mm.

The present invention is also directed to the present intraocular lens where the diameter of the optical portion is between 2.00 and 7.00 mm.

The inventors have undertaken a large scale scientific study to determine the parameters for the intervals of the present intraocular lens. Correlation between other parameters of the present intraocular lens has been determined by using different diopter values, diameters of the optic portion and heights of the body portion.

DETAILED DESCRIPTION OF THE FIGURES

A detailed description of the preferred embodiments of the present intraocular lens and methods for implanting such intraocular lenses follows with reference to the drawings.

Figure 1:
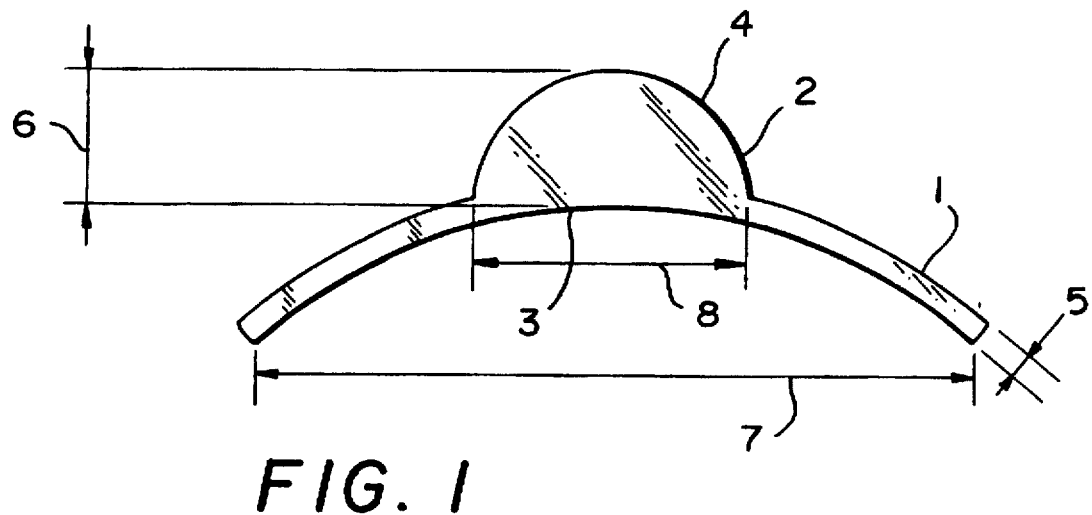
FIG. 1 is a sectional view of an intraocular lens according to the invention.

The intraocular lens of FIG. 1 is a first embodiment of the invention. The intraocular lens includes body portion 1 and optic portion 2. The posterior concave surface 3 of the body portion 1 forms the posterior surface of the intraocular lens. The radius of curvature of the posterior concave surface is the same as the radius of curvature of the anterior surface (17 in FIG. 3) of the natural crystalline lens of the eye. The anterior surface 4 of optic portion 2 is defined by a spherical surface of rotation. The thickness 5 of body portion 1 is between 0.3 and 0.98% of the thickness 6 of the intraocular lens that includes the thickness of the body portion 1 and optic portion 2. The thickness 6 of the intraocular lens is between 0.011 and 0.015% of the length 7 (measured as a secant of an arc between ends) of body portion 1. The diameter 8 of the optic portion is between 0.153 and 0.7% of the length 7 of body portion 1.

The ratio between the height of the body portion and the height of the intraocular lens itself can be no less that 0.30 because if it is, the intraocular lens will not fit in the posterior chamber and will traumatize the iris tissue. Further, if the value is greater than 0.98, correction of the hypermetropia is not effective.

The ratio between the thickness of the body portion and the height of the body portion cannot be less than 0.011, because if the ratio is less, the intraocular lens decentralizes and, if the ration is greater than 0.015, the intraocular lens traumatizes the tissue of the ciliary body.

The ratio between the height of the intraocular lens itself and the length of the body portion cannot be less than 0.095 because if the ratio is less than 0.095, or the ratio is greater than 0.192, correction of the hypermetropia is not effective.

The ratio between the diameter of the optic portion and the length of the body portion cannot be less that 0.153 because if it the ratio is less than 0.153 or greater than 0.7, correction of the hypermetropia is not effective.

Figure 2:
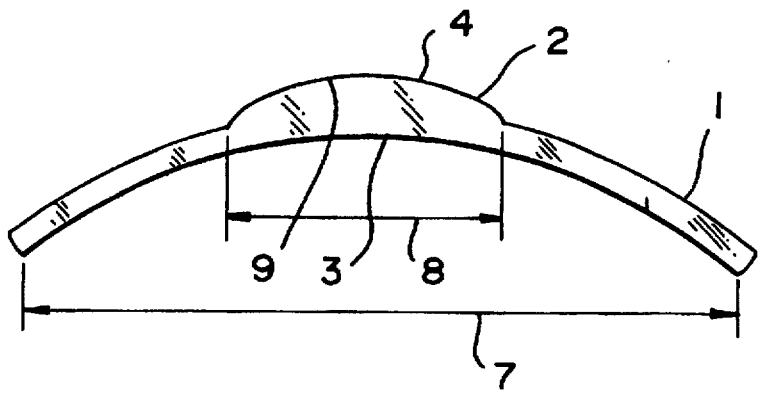
FIG. 2 is a sectional view of an alternative embodiment of the intraocular lens according to the invention.

FIG. 2 illustrates an embodiment of the invention, where the anterior surface 4 of optic portion 2 is characterized by a spherical impression 9. The radius of curvature of the anterior surface 4 of the optic portion 2 is between 0.29 and 0.967% of the radius of curvature of posterior surface 3 of the intraocular lens. Without spherical impression 9 the anterior surface 4 of optic portion 2 constitutes a surface of rotation of the second degree, e.g., a parabolic or ellipsoidal surface. In one embodiment, including spherical impression 9, anterior surface 4 constitutes a surface of rotation of the third degree. Further, the anterior surface 4 can be defined as a surface of rotation of higher degrees of rotation, i.e., a fourth degree and higher. The various forms of the anterior surface 4 compensate for spherical, chromatic and other aberrations of the natural eye.

In further embodiments of the invention, the intraocular lens is characterized by a concave posterior surface that forms an arc and a length 10 of the intraocular lens along a secant distance between ends of the arc is from 10 mm to 13 mm. Length 10 is defined as the secant distance between the ends of an arc formed by a concave posterior surface of an intraocular lens. In still another embodiment, the optic portion 2 has a diameter at its base of from 2.00 mm to 7.00 mm.

The diameter 11 of the optic portion cannot be less than 2.00 mm because if it is, a double passing of the light rays through the optic portion and body portion causes a double image and if the diameter 11 is greater that 7.00 mm, the intraocular lens would not fit inside the posterior (eye) chamber.

The length 10 of the body portion cannot be smaller than 10.00 mm because if it is, the eye falls into the category of microphthalmia and if the length 10 is greater than 13.00 mm, it is limited by the size of the ciliary sulcus in the posterior (eye) chamber.

Figure 3:
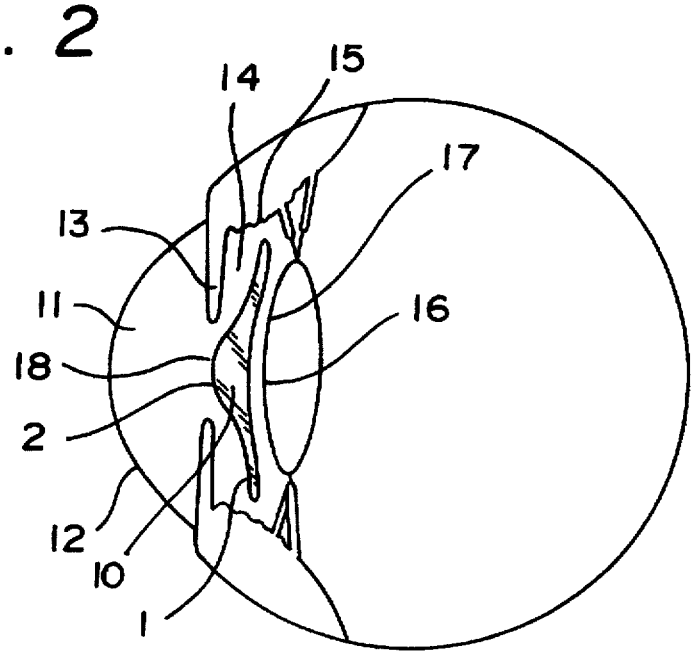
FIG. 3 is a partial sectional view of a human eye with an intraocular lens illustrating a lens implant according to the present invention.

FIG. 3 illustrate the present intraocular lens 10 implanted in a natural eye. The intraocular lens 10 can be implanted by forceps that hold the lens 10 and the lens is then inserted into the anterior chamber 11 of the eye through an incision in cornea 12. A spatula can be used to insert ends of body portion 1 through the iris 13 to posterior chamber 14. The peripheral ends of the body portion 1 are positioned against tissue of the ciliary body 15 with the posterior surface of the body portion 1 residing on an anterior surface of the natural crystalline lens 16. The intraocular lens is centered over the anterior surface 17 of the natural crystalline lens 16 so that the optic portion 2 is positioned into the pupil region 18. After the intraocular lens is implanted, a basal iridectomy is conducted at 19 and a continuous suture is applied to the cornea at 12.

The implanted lens is effective in correcting moderate to severe hypermetropia, for example from 4.00 to 10.00 diopters.

The following examples are intended to illustrate the invention without limiting its scope.

EXAMPLES

Example 1

The patient P., 18 years of age. Diagnosis: Hypermetropia of high level of right eye. Amyblyopia of high level of the right eye. Anisometropia.

Visual acuity OD0.125 sph+7.5 cyl.–0.5 ax 25=0.4

Surgery performed—implantation of a proposed IOL of an appropriate diopter.

Post-surgery period free of complications.

Upon leaving the hospital (on the sixth day)—visual acuity: 0.4 without correction. Eye — normal, position of IOL—correct, lens—transparent, angle of the anterior chamber—open.

Examination data OD, four months post-operative.

Visual activity 0.6 without correction.

Example 2

The patient K., 20 years of age. Diagnosis: Hypermetropia of high level of both eyes.

Visual acuity OD 0.05 sph+9.50=0.40

OS 0.20sph+9.00=0.90

Surgery performed—implantation of a proposed IOL of an appropriate diopter (for the specific patient).

Post-surgery period free of complications. Upon leaving hospital (on the third day after surgery)—visual acuity: 0.9 without correction. Eyes—normal, position of IOL—correct, lens transparent, angle of the anterior chamber—open.

Examination data OU a year after the operation (took place).

Visual acuity OU 1.00 without correction.

Clinical approbation of the presented artificial lens has shown that the given design represents a highly effective artificial eye lens which can be used in the surgical correction of hypermetropia from 4.00 to 10.00 diopters.

Other modifications and equivalents of the invention will occur to those skilled in the art. These modifications and equivalents thereof are intended to be included within the scope of this invention.

What is claimed is:

1. An intraocular lens comprising:

a body portion and an optic portion, wherein:

(1) a thickness of said body portion is from 0.3 to 0.98% of a thickness of the intraocular lens including the combined thicknesses of the body portion and the optic portion, and from 0.011 to 0.015% of a length of the body portion, the length being defined by the secant of an arc between opposed edges of the body portion;

(2) a thickness of the intraocular lens including the combined thicknesses of said body portion and said optic portion is from 0.095 to 0.192% of said length of said body portion; and (3) a diameter of said optic portion is from 0.153 to 0.7% of said length of said body portion.

2. An intraocular lens comprising:

a body portion; and an optic portion, said intraocular lens comprising:

(1) a ratio of a thickness of said body portion to a thickness of said intraocular lens including the combined thicknesses of the body portion and the optic portion, of from 0.3 to 0.98:1;

(2) a ratio of a thickness of said body portion to a length of said body portion of from 0.011 to 0.015:1, said length being defined by the secant of an arc between opposed edges of the body portion;

(3) a ration of a thickness of said intraocular lens including the combined thickness of said body portion and said optic portion, to said length of said body portion of from 0.095 to 0.192:1; and (4) a ratio of a diameterof said optic portion to said length of said body portion of 0.153 to 0.7:1.

3. The intraocular lens of claim 1, wherein said optic portion comprises an anterior surface defined by a surface of rotation of the first degree.

4. The intraocular lens of claim 3, wherein said anterior surface is defined by a spherical surface of rotation.

5. The intraocular lens of claim 1, wherein said optic portion comprises an anterior surface defined by a surface of rotation of the second degree.

6. The intraocular lens of claim 5, wherein said anterior surface is defined by a parabolic surface of rotation.

7. The intraocular lens of claim 5, wherein said anterior surface is defined by an ellipsoidal surface of rotation.

8. The intraocular lens of claim 1, wherein said optic portion comprises an anterior surface defined by a surface of rotation of the third degree.

9. The intraocular lens of claim 1, wherein said optic portion comprises an anterior surface having a radius of curvature of from 0.29 to 0.967% of a radius of curvature of a posterior surface of said intraocular lens.

10. The intraocular lens of claim 8, wherein said optic portion comprises a convex anterior surface and said intraocular lens comprises a concave posterior surface.

11. The intraocular lens of claim 1, wherein said length of said body portion is from 10 mm to 13 mm.

12. The intraocular lens of claim 1, wherein said optic portion has a diameter of from 2.00 mm to 7.00 mm.

13. The intraocular lens of claim 1, wherein said body portion has a thickness of about 0.15 mm.

14. An intraocular lens, comprising:
a body portion and an optic portion, wherein said optic portion comprises an anterior surface having a radius of curvature between 0.29 and 0.967% of a radius of curvature of a posterior surface of said intraocular lens.

15. The intraocular lens of claim 14, wherein said anterior surface is convex and said posterior surface is concave.

16. The intraocular lens of claim 15, wherein said concave posterior surface forms an arc; and a length of said body portion along a secant distance of said arc is from 10 mm to 13 mm.

17. The intraocular lens of claim 14 wherein said optic portion has a diameter of from 2.00 mm to 7.00 mm.

18. The intraocular lens of claim 14, wherein said body portion has a thickness of about 0.15 mm.

19. The intraocular lens of claim 14, wherein said optic portion comprises an anterior surface defined by a surface of rotation of the first degree.

20. The intraocular lens of claim 18, wherein said optic portion comprises an anterior surface defined by a spherical surface of rotation.

21. The intraocular lens of claim 14, wherein said optic portion comprises an anterior surface defined by a surface of rotation of the second degree.

22. The intraocular lens of claim 18, wherein said optic portion comprises an anterior surface defined by a parabolic surface of rotation.

23. The intraocular lens of claim 18, wherein said optic portion comprises an anterior surface defined by an ellipsoidal surface of rotation.

24. The intraocular lens of claim 14, wherein said optic portion comprises an anterior surface defined by a surface of rotation of the third degree.

25. A method of implanting an intraocular lens into an eye of a patient to correct hypermetropia, comprising the steps of:
providing an intraocular lens comprising a body portion and an optic portion, wherein (1) a thickness of said body portion is from 0.3 to 0.98% of a thickness of said intraocular lens including the combined thicknesses of said body portion and said optic portion, from 0.011 to 0.015% of a length of said body portion, said length being defined by the secant of an arc between opposed edges of said body portion; (2) the thickness of said intraocular lens from 0.095 to 0.192% of said length of said body portion; and (3) a diameter of said optic portion is from 0.153 to 0.7% of said length of said body portion; and
inserting said intraocular lens into said eye of said patient, wherein said hypermetropia is corrected.

26. The method of claim 25, wherein said eye comprises: an anterior chamber, a posterior chamber, a cornea anterior to said chambers, an iris between the anterior chamber and the posterior chamber defining a pupil region, a ciliary body within the posterior chamber and a natural crystalline lens within the posterior chamber.

27. The method of claim 26, wherein said step of inserting comprises:
a. inserting said intraocular lens into the anterior chamber of the eye through an incision in the cornea of the eye;
b. inserting ends of said body portion through the iris; and
c. positioning peripheral ends of said body portion against tissue of the ciliary body with a posterior surface of said body portion residing on an anterior surface of the natural crystalline lens.

28. The method of claim 26, wherein said step of inserting comprises: inserting said intraocular lens into said posterior chamber of said eye to a position anterior to a natural crystalline lens of said eye.

29. The method of anyone of claims 27 or 28 comprising: centering said intraocular lens over said natural crystalline lens so that said optic portion is positioned into the pupil region.

30. The method of claim 29, further comprising: conducting a basal iridectomy; and applying a continuous suture to the cornea of the eye.

31. The method of any one of claims 27 or 28, wherein said optic portion comprises an anterior surface having a radius of curvature from 0.29 to 0.967% of a radius of curvature of a posterior surface of said intraocular lens.

32. A method of implanting an intraocular lens into an eye of a patient to correct hypermetropia, comprising the steps of:
providing an intraocular lens comprising a body portion and an optic portion, wherein said optic portion comprises an anterior surface having a radius of curvature from 0.29 and 0.967% of a radius of curvature of a posterior surface of said intraocular lens; and
inserting said intraocular lens into said eye anterior to a natural crystalline lens of said eye of said patient, wherein said hypermetropia is corrected.

33. The method of claim 32, wherein said eye comprises: an anterior chamber, a posterior chamber, a cornea anterior to said chambers, an iris between the anterior chamber and the posterior chamber defining a pupil region, a ciliary body within the posterior chamber and a natural crystalline lens within the posterior chamber.

34. The method of claim 33, wherein said step of inserting comprises:
a. inserting the intraocular lens into the anterior chamber of the eye through an incision in the cornea of the eye;
b. inserting ends of said body portion through the iris; and
c. positioning peripheral ends of said body portion against tissue of the ciliary body with a posterior surface of said body portion residing on an anterior surface of the natural crystalline lens.

35. The method of claim 33, wherein said inserting comprises: inserting said intraocular lens into said posterior chamber of said eye to a position anterior to said natural crystalline lens of said eye.

36. The method of any one of claims 34 or 35, further comprising: centering said intraocular lens over the said natural crystalline lens so that said optic portion is positioned into said pupil region.

37. The method of claim 36, further comprising conducting a basal iridectomy and applying a continuous suture to the cornea of the eye.

38. A method of surgically correcting moderate to severe hypermetropia in the eye of a patient suffering therefrom, comprising:

implanting an intraocular lens comprising a body portion and an optic portion, into a posterior chamber of said patients eye to a position anterior to a natural crystalline lens of said eye, wherein said intraocular lens correct hypermetropia in said patient suffering therefrom from 4.00 to 10.00 diopters.

* * * * *